United States Patent [19]
Harrison

[11] 4,325,361
[45] Apr. 20, 1982

[54] DEEP HEATING ELECTRODE

[75] Inventor: William H. Harrison, Woodland Hills, Calif.

[73] Assignee: Donald L. Morton & Associates, Pacific Palisades, Calif.

[21] Appl. No.: 36,223

[22] Filed: May 4, 1979

Related U.S. Application Data

[62] Division of Ser. No. 854,730, Nov. 25, 1977, Pat. No. 4,186,729.

[51] Int. Cl.³ .............................................. A61N 1/42
[52] U.S. Cl. .................................... 128/1.3; 128/804; 219/10.79; 336/66
[58] Field of Search ................. 128/1.3–1.5, 128/804, 419 R; 219/10.79; 336/66

[56] References Cited

U.S. PATENT DOCUMENTS

| | | | |
|---|---|---|---|
| 2,477,118 | 7/1949 | Detuno | 219/10.79 |
| 2,478,640 | 8/1949 | Roberds | 219/10.79 X |
| 2,714,648 | 8/1955 | Blok et al. | 219/10.79 |
| 2,788,426 | 4/1957 | Thompson | 219/10.79 X |
| 2,790,055 | 4/1957 | Iperan | 219/10.79 |
| 2,999,977 | 9/1961 | Brown | 219/10.79 X |
| 3,368,565 | 2/1968 | Kendall et al. | 128/804 |
| 3,633,588 | 1/1972 | Haas | 128/804 |
| 3,991,770 | 11/1976 | LeVeen | 128/804 |
| 4,008,762 | 2/1977 | Fisher et al. | 219/10.79 X |

FOREIGN PATENT DOCUMENTS

| | | | |
|---|---|---|---|
| 599372 | 3/1948 | United Kingdom | 219/10.79 |
| 712132 | 7/1954 | United Kingdom | 219/10.79 |
| 1111035 | 4/1968 | United Kingdom | 219/10.79 |

*Primary Examiner*—Lee S. Cohen
*Attorney, Agent, or Firm*—Poms, Smith, Lande & Rose

[57] ABSTRACT

The present invention discloses an improved electrode for use with apparatus employing radio frequency energy for deep heating of materials. In particular, it is adapted for the medical treatment of living animal tissue by hyperthermia. The electrode comprises a single loop turn having capacitance associated therewith so as to resonate the electrode for maximum power transfer thereto. The electrode causes a field to be generated within the annular region enclosed by the electrode comprising a plurality of concentric, substantially equally powered lines of force in which the living tissue to be treated is disposed. The electrode finds particular use in the treatment of deep seated cancers in patients.

2 Claims, 12 Drawing Figures

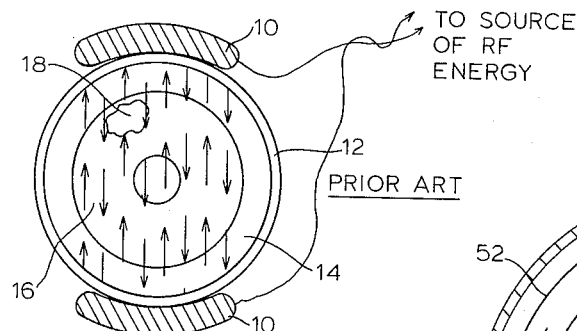
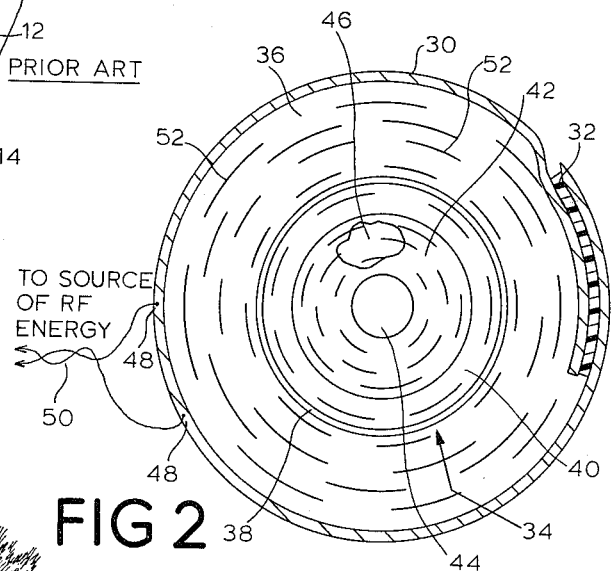
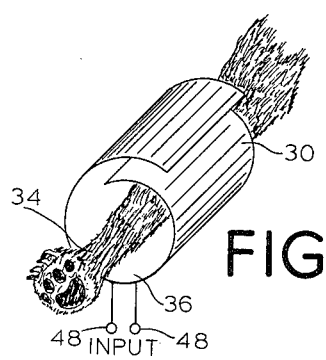
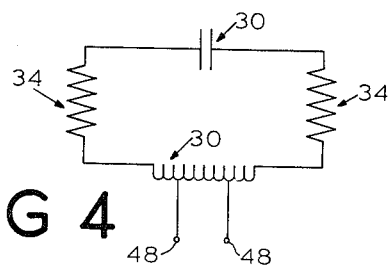
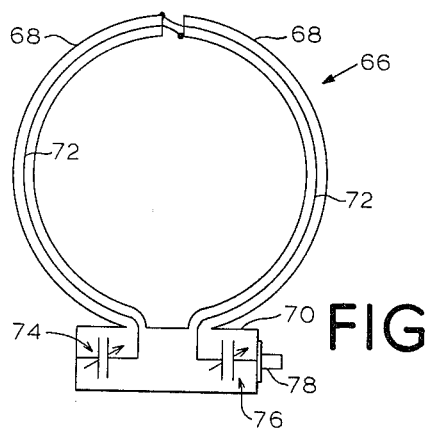
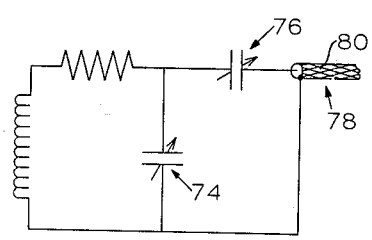

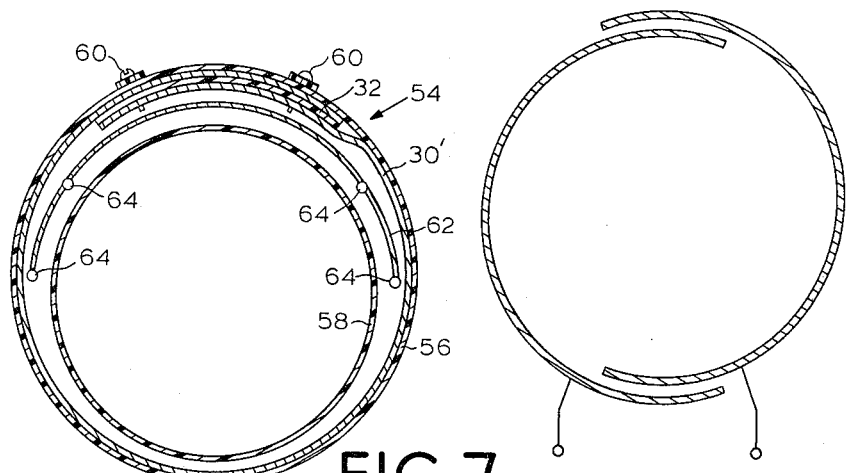
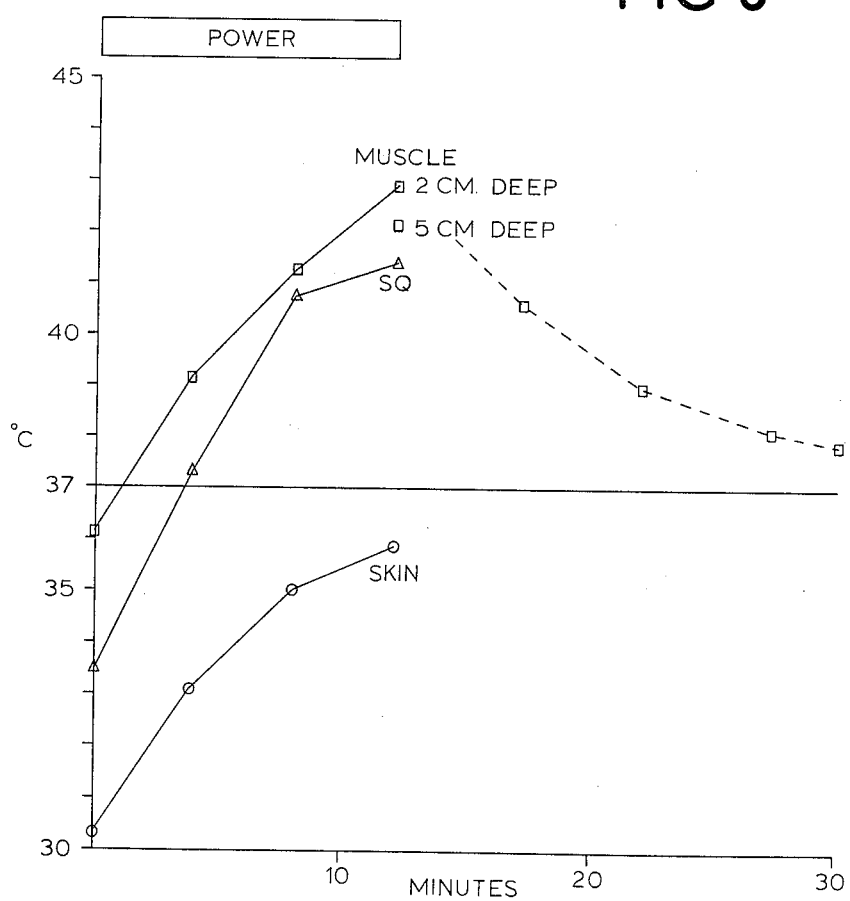

DEEP HEATING ELECTRODE

This is a division, of application Ser. No. 854,730, filed Nov. 25, 1977, now U.S. Pat. No. 4,186,729.

BACKGROUND OF THE INVENTION

The present invention relates to electrodes used in the transfer of radio frequency energy to a substance and more particularly to electrodes used in the medical treatment of living tissue in animals by hyperthermia techniques.

It has been well known for sometime that many substances, including animal tissue, respond by heating to the passing of radio frequency (RF) energy therethrough. In particular, this has found application in the selective destruction of certain tissues within living animals including humans. More specifically, it has been found that because tumors (both malignant and benign) have a reduced capacity for the passage of blood therethrough with attendant cooling thereby, the application of RF energy to the tumor and the surrounding tissue will cause the tumor to be elevated to a higher temperature than the surrounding tissue. It is possible, by careful control of the RF energy applied, to raise the temperature of the tumor above the point were necrosis of the tumor will occur while maintaining the temperature of the healthy surrounding tissue below the destructive temperature level. By such a technique, the tumor is destroyed while the surrounding healthy tissue is undamaged.

It has been common practice in the prior art employing such techniques to connect a pair of paddle type electrodes to a source of RF energy. The electrodes are then disposed on either side of the tissue containing the tumor in the manner shown in FIG. 1. The RF energy passes between the electrodes 10 with the tissue containing the tumor behaving in a manner of a dielectric in a capacitor. Ordinarily, the tissue placed between the electrodes is a complex substance with varying resistances such that those components with the greatest resistance (e.g. skin 12 and subcutaneous tissue 14) are preferentially heated, while those components with lower resistance and those more deeply located (e.g. muscle 16 and the tumor 18) are least heated. In practice, this generally results in the inability to heat deeply, or in superficial heat absorption which results in burning. Since tumors and various disease states potentially treatable by heat are often located deep within the body, a method and apparatus for allowing deep heating without skin and subcutaneous tissue injury would be desirable. To date, with the apparatus of the prior art, the only method for treatment of deeply located tissues by hyperthermia was through the surgical implantation of the electrodes. That is, the tissue to be treated is surgically exposed so that the paddle type electrodes can be disposed on either side and close adjacent to the area of treatment.

A spiral, pancake type coil has also been used commercially. It produces a localized magnetic field which attenuates very rapidly with spacing from the body. It also has a large voltage build-up between turns thus creating a related voltage gradient across the skin surface in that region. The result is superficial heating in the skin and subcutaneous fat layer. Such an electrode is, therefore, of little value in deep medical treatment by hyperthermia.

Wherefore, it is the object of the present invention to provide an electrode for use in medical treatment by hyperthermia which allows deep heating by the transfer of radio frequency energy without the attendant hazards to healthy tissues described above.

SUMMARY OF THE INVENTIONS

The foregoing objectives have been accomplished by the present invention wherein the deep heating of animal tissue is accomplished by placing the animal tissue in non-contacting relationship within a substantially annular region defined by an electrode; and, exciting the electrode with radio frequency energy to establish a magnetic field comprising a plurality of concentric electrostatic field lines of similar magnitude within the annular region whereby the tissue is heated throughout. The electrode disclosed herein comprises a strip of electrically conductive material disposed to form a single turn loop of substantially annular shape and means for coupling a supply of radio frequency energy into the electrode disposed in operable relationship with the strip of material. In the preferred embodiment shown, the strip has the ends thereof over-lapped in non-contacting, spaced relationship and has a dielectric material disposed between the over-lapped ends. The dielectric material, the distance of the spacing between the over-lapped ends and the area defined by the over-lapping of the ends are such in relationship to the diameter of the annular shape that the capacitive reactance of the over-lapped ends is equal to the inductive reactance of the loop.

DESCRIPTION OF THE DRAWINGS

FIG. 1 is a simplified drawing of two paddle type electrodes according to the prior art as used in hyperthermia techniques.

FIG. 2 is a simplified drawing of the operation of the electrode of the present invention.

FIG. 3 is a simplified drawing of the electrode of the present invention as used in the deep heating of an animal extremity.

FIG. 4 is a drawing of the equivalent circuit of the electrode of the present invention.

FIG. 6 is a graph of the temperatures reached in the various tissue components of a human thigh by using a ten inch diameter electrode according to the present invention.

FIG. 7 is a more detailed drawing of the construction of the preferred embodiment of the present invention.

FIG. 8 is a simplified drawing of the construction of a twenty inch diameter electrode according to the present invention used in treatment of a human torso.

FIG. 11 is a simplified drawing of an alternate embodiment of the electrode of the present invention.

FIG. 12 is a drawing of the equivalent circuit of the electrode of FIG. 11.

DESCRIPTION OF THE PREFERRED EMBODIMENT

Figure 9:
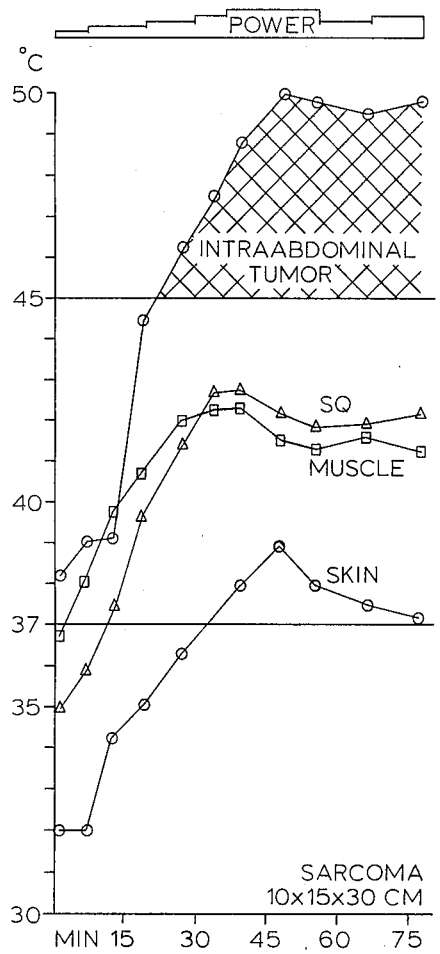
FIG. 9 is a graph of temperatures reached in treating an intra-abdominal tumor with the electrode of FIG. 8.

In my coopending application entitled "Impedance Matched Hyperthermia Apparatus", filed on even date herewith, (now abandoned), I have disclosed an impedance matching network for supplying an electrode employed in hyperthermia apparatus with radio frequency (RF) energy with maximum power transfer by employing a balanced, floating, secondary circuit to which the electrode is attached. The impedance matching network described therein provides superior results with the present electrode as it did with the conventional paddle type electrodes described in that application. Accordingly, said network has been employed in testing the electrodes disclosed herein and its use is preferred and recommended in conjunction with these electrodes. The test results disclosed hereinafter were accomplished using such an impedance matching network in conjunction with each electrode.

The basic principle of the present invention is shown with reference to FIGS. 2, 3, and 4. The electrode 30 comprises a strip of conductive material formed into a cylinder having the ends thereof in overlapping, noncontacting relationship. While an air dielectric could be employed, it is preferred that a material such as polytetrafluoroethylene be disposed between the overlapping ends of electrode 30 such as that labeled 32 in FIG. 2. The first tested embodiment of the present invention was configured such as the electrode 30 of FIG. 2 having a diameter of 10 inches such that an extremity of an animal 34 could be disposed within the annular region 36 defined by electrode 30 in the manner of FIG. 3. In simplified form, the animal extremity 34 would appear as shown in FIG. 2 as comprising skin 38, subcutaneous tissue 40, muscle 42, and bone 44. A tumor 46 to be treated is shown as being disposed therein.

Electrode 30 is provided with means for coupling a supply of RF energy into the electrode. One method employed was the providing of taps 48 to which a connector 50 providing the RF energy can be connected. When electrode 30 is connected to a source of RF energy, a plurality of concentric electrostatic field lines 52 are formed within annular region 36. The equivalent circuit is shown in FIG. 4. The inductance and capacitance are attributable to the single turn loop of electrode 30 and the overlapped ends having dielectric material therebetween respectively. The resistance is virtually entirely due to the animal extremity 34 within annular region 36. Thus, it can be seen, that if the capacitive reactance of the overlapped ends is made equal to the inductive reactance of the single turn loop by adjusting the amount of overlap (and thereby the total area of overlap), the spacing between the overlapped surfaces, and the dielectric material disposed therebetween, the circuit can be placed in resonance whereby a resistive load will be presented to the RF source so that maximum power will be transferred to the resistive load, e.g. the tissue of the animal extremity 34.

Figure 5:
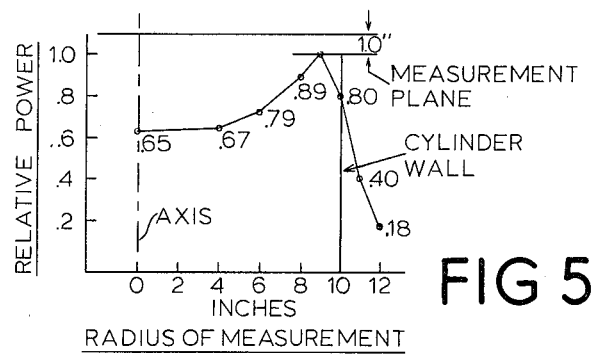
FIG. 5 is a graph of the power level across the annular region enclosed by a 20 inch diameter electrode according to the present invention.

Referring briefly to FIG. 5, actual power measurements taken with a 20 inch diameter tested embodiment of the present invention as a function of the distance from the center of the electrode are shown. It can be seen from FIG. 5 that the power level from the center out to approximately 4+ inches is substantially constant. If an extremity is disposed coaxially with electrode 30 of FIG. 2 within an annular region extending from the center axis and less than a radius of 5 inches, the entire extremity from the surface to the center thereof will be subject to a substantially constant electrostatic field of power. Note that contrary to the prior art configuration of FIG. 1, the field lines 52 do not have to pass through the skin 38 and subcutaneous tissue 40 to reach the tumor 46 with attendant losses. Rather, each layer within the extremity 34 is subjected to its own electrostatic field lines 52 which are affecting only that layer.

The 10 inch diameter electrode was designed to encircle a human limb. FIG. 6 illustrates the thermal characteristics achieved on a human thigh. Power (250 watts) was applied in 3 minute increments with 1 minute off intervals for temperature measurements. Temperature of skin, subcutaneous fat and deep muscle were recorded by insertion of a needle thermistor probe during the off time. The important significance of this data is that the deep muscle tissue is uniformly heated to the highest temperature, while maintaining lower subcutaneous fat temperatures and very low skin temperatures. No cooling of any kind was used. The principle of creating concentric electrostatic field lines within the resonant cylindrical electrode and within the thigh was thus established. Further test results employing the electrode to treat a tumor located deep within the body, below the fat layers, will be discussed hereinafter.

Referring now to FIG. 7, further details of the actual construction of electrode 30 shown previously in simplified form in FIG. 2 are shown. The complete electrode indicated generally as 54 comprises a 5 inch wide strip of conductive material 30' having the ends thereof overlapped with dielectric material 32 disposed therebetween. In the actual embodiment, dielectric material 32 consists of a 0.032 inch thick polytetrafluoroethylene sheet. The metallic cylinder comprising conductive material 30' and dielectric material 32 is disposed within an outer plastic cylinder 56 and an inner plastic cylinder 58 providing an insulation so that direct patient contact with the electrode is prevented. In the preferred embodiment, the overlapped ends of conductive material 30' comprising the capacitor plates and the dielectric material 32 are held together by insulated screws 60 passing through the outer plastic cylinder 56. While tapped coupling as shown in the simplified drawing of FIG. 2 was successfully employed, the preferred method of coupling the RF energy to the electrode is through inductive coupling employing a close-spaced half turn of number 12 wire 62 located at one end of the cylinder. Provisions are made to vary the coupling by providing intermediate taps 64 on the half turn coupling wire 62.

A 20 inch diameter cylindrical electrode was designed to encompass the human torso for the purpose of heating a large part of the body. A cylinder 10 inches long was chosen to meet the physical needs and to optimize the electrical characteristics. The cylinder sections overlap at two places as shown in the simplified drawing of FIG. 8. This double overlapping forms two capacitors which have a total series reactance equal to the inductive reactance. Thus, each capacitor must have a value twice that required if only one capacitor were used to resonant the cylinder. The use of multiple overlapping is done because the voltage build-up at the capacitors can be minimized by the use of multiple capacitors in series around the circumference, i.e. minimizing the undesired capacitive coupling. With the cylinder mounted over the human torso, it was found that excellent coupling to the body is achieved producing a loaded Q of approximately 20. The equivalent resonant circuit resistance is then conveniently transformed to a 50 ohm input by tapping across one of the capacitors, as shown in FIG. 8.

Figure 10:
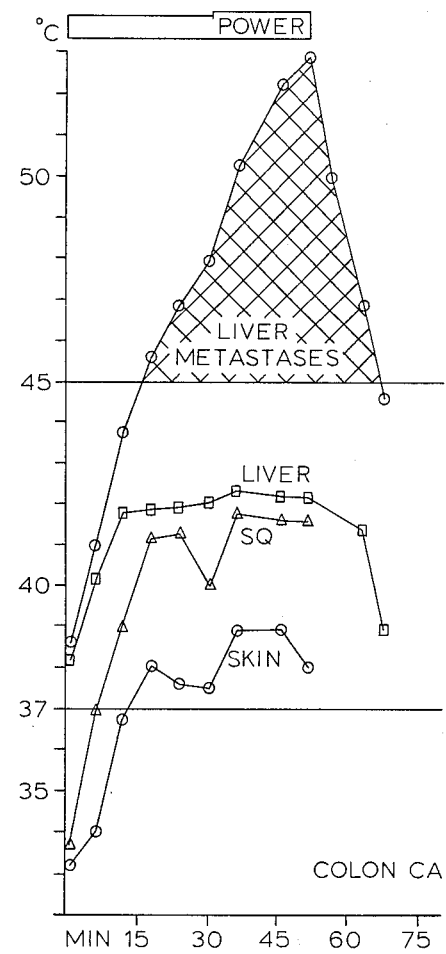
FIG. 10 is a graph of temperatures reached in treating a liver metastases with the electrode of FIG. 8.

The temperature profile of a patient produced by employing the 20 inch diameter electrode just described is shown in FIG. 9. The patient had a large intra-abdominal sarcoma, i.e. a primary tumor. Sufficient power was applied to raise the tumor temperature to approximately 50° C. while maintaining healthy tissue temperatures at 43° C. and below. Because of the poor blood flow in the tumor, previously described, it is possible to raise the tumor temperature to lethal levels while not causing damage to healthy tissue as shown. In this case, power was gradually increased from 250 watts to 750 watts. As may be seen, from FIG. 9, the tumor temperature is maintained above 49° C. for 35 minutes. Another patient with a large secondary tumor, liver metastases was treated using the 20 inch diameter electrode. The temperature profile results from this treatment are shown in FIG. 10. In this case, temperature measurements were made of the liver metastases, normal liver, subcutaneous fat and skin. The healthy tissue, including the liver, remained at acceptable temperature levels while the tumor again achieved lethal temperatures. Biopsy after three weekly similar treatments showed that complete necrosis has occurred.

An alternate embodiment of the electrode of the present invention is shown in FIG. 11 with its equivalence circuit shown in FIG. 12. The electrode of FIG. 11 generally indicated at 66 is in the form of a 15 inch diameter loop fabricated from one half inch thin wall copper tubing. The two semi-annular copper conduits 68 are connected on one end thereof into a metallic shield box 70 to form the 15 inch diameter loop. The opposite ends of the copper conduit 68 not fastened to the shield box 70 are disposed in close adjacent spaced relationship. A pair of electrical conductors (in this case, #12 polytetrafluoroethylene covered wire) 72 is passed one each through each of the copper conduits 68. On the ends emerging from the copper conduits 68 away from shield box 70, each wire 72 is connected to the opposite conduit 68 in the manner shown of FIG. 11. The other end of one wire 72 emerging from one of the copper conduits 68 is connected to a first variable capacitor 74 which is then connected to shield box 70. The other wire 72 in the other copper conduit 68 is connected on its other end to a second variable capacitor 76 which in turn is connected to the center connector of a coaxial connector 78 which in turn is connected on its opposite side to shield box 70. With a coaxial cable 80 connected to coaxial connector 78, the equivalent circuit appears as in FIG. 12. When employing the electrode of FIG. 11, the loop inductance is brought into resonance by capacitor 74. By subsequent proper adjustment of both capacitors 74 and 76, the circuit impedance can be matched to the typical 50 ohm power source.

Thus, it can be seen from the foregoing description that the present invention provides an electrode particularly well adapted for magnetically coupling RF energy into the human body for the purpose of heating at any depth. Previous attempts to raise the temperature deep within the body, while partially successful, have usually suffered from excessive heating of the skin and subcutaneous fat layer. Researchers have shown that fat has a much higher resistance than muscle tissue, i.e. approximately 2,000 to 3,000 ohm-centimeters and 100 to 150 ohm-centimeters respectively. Power consumed follows the relationship $P = I^2R$. Since in the prior art the fat and muscle layers essentially in series between the electrodes, the current I, is constant and the power consumed is directly proportional to I. The magnetic electrode of the present invention completely surrounds the body or limb to be treated and establishes a relatively uniform magnetic field in the surrounded region. It is purposely spaced away from the body to minimize magnetic field variation as well as essentially eliminating the undesired electrostatic coupling normally employed. The magnetic field thus produced within the body establishes concentric electrostatic field lines of similar magnitude. Since E-field lines are now concentric within the cylindrical electrode, they do not have to pass through the subcutaneous fat layer to excite the muscle region. The design parameters described heretofore are for the medical frequency 13.56 MHz. The same principles apply to both 27.12 and 40.68 MHz medical frequencies as well, by scaling the inductance and capacitive parameters.

It is to be understood that while the present electrode is primary directed to and the tested embodiments and test results described are in relation to the medical treatment of tumors in human subjects, the electrode can be equally well used in any application wherein deep heating of a substance, be it animal tissue or otherwise, is desired.

Having thus described my invention, I claim:

1. An electrode for use in the destruction of tumors in living animal tissue by hyperthermia comprising:
   (a) a shield box of a conductive material;
   (b) a pair of electrical connectors for attaching a source of radio frequency energy carried by said box, one of said electrical connectors being electrically connected to said box;
   (c) a pair of semi-annular conduits of an electrically conductive material each electrically connected on one end thereof to said shield box and communicating with the interior thereof, said pair of conduits being disposed to form a substantially annular shape with the other ends thereof in close adjacent spaced relationship;
   (d) a pair of electrical conductors disposed coaxially within respective ones of said conduits and insulated therefrom from respective first ends disposed within said shield box to respective second ends exiting said close adjacent spaced ends of said conduits, each conductor being electrically connected on said second end to said spaced end of said conduit in which it is not coaxially disposed;
   (e) a first variable capacitor electrically connected between one of said first ends of said pair of conductors and said shield box; and,
   (f) a second variable capacitor electrically connected between the other of said first ends of said pair of conductors and the one of said pair of connectors not electrically connected to said box.

2. An electrode for use in the treatment of animal tissue by hyperthermia comprising:
   (a) electrically conductive material operably disposed to form a single turn loop of substantially annular shape; and
   (b) means for coupling a supply of radio frequency energy into said electrode disposed in operable relationship with said electrically conductive material, said coupling means including adjustable means for placing said single turn loop in resonance; wherein,
   (c) said electrically conductive material comprises a plurality of segments of shielded conductor, each of said segments having an outer shield of electrically conductive conduit and an inner electrically conductive wire disposed within said conduit and insulated therefrom, said segments being arcuate in shape and disposed in close spaced end-to-end relationship with one another to form a substantially annular shape, said inner electrically conductive wire at each end of each of said plurality of segments being electrically connected to said electrically conductive conduit next adjacent thereto at each point of said end-to-end relationship except at one such point so as to leave at said one point a first available end of said electrically conductive wire in association with a first end of said electrically conductive conduits and a last available end of said electrically conductive wire in association with a last end of said electrically conductive conduits; and wherein said coupling means comprises, (d) a shield box of conductive material, said first and last ends of said electrically conductive conduits being electrically connected to said shield box, said first and last available ends of said electrically conductive wires passing in insulated relationship within said shield box into the interior of said shield box;

(e) a pair of electrical connectors for attaching a source of radio frequency energy carried by said shield box, one of said connectors being electrically connected to said box;

(f) a first variable capacitor electrically connected between said first available end of said electrically conductive wires and said shield box; and, (g) a second variable capacitor electrically connected between said last available end of said electrically conductive wires and the one of said pair of electrical connectors not electrically connected to said box.

* * * * *